United States Patent [19]

Baker et al.

[11] Patent Number: 5,310,680
[45] Date of Patent: May 10, 1994

[54] TEST FOR FECAL OCCULT BLOOD

[75] Inventors: Josefina T. Baker, Cupertino; Peter U. Ly, San Jose; Eli Z. Olivet, Sunnyvale, all of Calif.

[73] Assignee: Smithkline Diagnostics, Inc., San Jose, Calif.

[21] Appl. No.: 23,133

[22] Filed: Feb. 24, 1993

Related U.S. Application Data

[63] Continuation of Ser. No. 681,489, Apr. 3, 1991, abandoned, which is a continuation of Ser. No. 96,995, Sep. 16, 1987, abandoned.

[51] Int. Cl.$^5$ .............................................. G01N 33/72
[52] U.S. Cl. ....................................... 436/66; 435/28; 436/135
[58] Field of Search ........................... 436/66, 67, 135; 435/28; 252/186.34, 364

[56] References Cited

U.S. PATENT DOCUMENTS

| | | |
|---|---|---|
| 3,290,117 | 12/1966 | Adams . |
| 4,017,261 | 4/1977 | Svoboda et al. ............... 436/66 |
| 4,220,713 | 9/1980 | Rittersdorf ...................... 436/66 |
| 4,247,631 | 1/1981 | Nix et al. ......................... 436/66 |
| 4,290,773 | 9/1981 | Magers . |
| 4,302,537 | 11/1981 | Gundermann et al. ........ 436/66 |
| 4,333,734 | 6/1982 | Fleisher . |
| 4,460,684 | 7/1984 | Bauer ............................... 435/28 |
| 4,486,536 | 12/1984 | Baker ............................... 436/66 |
| 4,493,892 | 1/1985 | Fleisher ........................... 435/38 |
| 4,778,753 | 10/1988 | Yamanishi et al. ............. 436/66 |
| 4,828,983 | 0/0000 | McClune . |

Primary Examiner—Timothy M. McMahon
Attorney, Agent, or Firm—William H. May; Gary T. Hampson; Janis C. Henry

[57] ABSTRACT

Improved fecal occult blood test having a matrix such as paper printed or impregnated with guaiac. The improvement comprises increasing the sensitivity while maintaining or improving the specificity of the test by employing an alcoholic peroxide developing solution which contains an enhancing agent. The enhancers comprise phenolic type compounds such as esters of parahydroxybenzoic acids.

6 Claims, No Drawings

TEST FOR FECAL OCCULT BLOOD

This is a continuation of copending application Ser. No. 07/681,489 filed on Apr. 3, 1991 now abandoned which is a continuation of Ser. No. 07/096,955 filed on Sep. 16, 1987 now abandoned.

This invention relates to an improved fecal occult blood test which increases the sensitivity while improving or maintaining the specificity of the test. More particularly, it relates to an improved hydrogen peroxide developing solution for fecal occult blood tests.

BACKGROUND OF INVENTION

Specimen test slides and procedures for detecting occult blood in fecal matter are well known. For example, U.S Pat. No. 3,996,006 discloses slides having a specimen receiving sheet between a front panel and a rear panel with openings in the front and rear panels and pivotal covers or flaps to cover these openings. One such test slide is sold under the trademark of 'Hemoccult'.

The specimen receiving sheet is generally an absorbent paper impregnated with a guaiac reagent. The hemoglobin catalyzed oxidation of the guaiac extract coated paper is used clinically to detect occult blood in feces. Briefly, the test procedure is as follows.

A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue. The overall reaction is a follows:

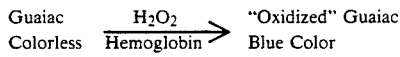

One of the problems associated with this test is the number of false negatives, i.e., negative test results in samples of known bleeding patients. The test is not sensitive enough to pick up lower levels of blood in the feces.

Another disadvantage of the guaiac test is that other non hemoglobin type compounds present in the stool, such as peroxidases present in certain foods, will also catalyze the oxidation of guaiac and result in a blue color. This results in false positive reaction, i.e., a positive reaction without fecal occult blood present.

Previous attempts have been made to increase the sensitivity of the present Hemoccult ® test. Hydration of the smear prior to development is often employed. However, while hydration produces a more sensitive test the method also adversely affects the specificity of the test. It produces unacceptable high false positive rates by reacting with other interfering substances such as vegetable peroxidases.

It is therefore the object of this invention to increase the sensitivity of the test while improving or maintaining the specificity of the current Hemoccult ® test. Increasing the sensitivity includes detecting lower levels of blood in the feces and obtaining greater readability, i.e., obtaining a clearer and deeper blue color with the same concentrations.

Briefly, this invention consists of an improved developing solution for determining fecal occult blood in a sample using a test matrix containing guaiac. The solution comprises an alcoholic solution of hydrogen peroxide and certain enhancing agents. The developer is largely alcoholic, containing a minimum amount of water. It was unexpectedly discovered that when these enhancing agents were added to the developing solution a more intense and readable blue color end point resulted than obtained in the current fecal occult blood tests. Further, the novel solution of this invention degrades and inhibits the more labile peroxidases which also catalyze the oxidation and produce the same color change.

The enhancers employed in this invention comprise phenolic type compounds. Examples of such enhancers are esters of hydroxybenzoic acid such as methyl, ethyl, propyl, butyl, benzyl, and phenyl parahydroxybenzoates. Preferably the lower alkyl esters of p hydroxybenzoic acid having from 1 to 4 carbon atoms, also known as parabens, are employed in this invention. Other examples of enhancers are phenol, guaiacol, p hydroxybenzoic acid, 3,5-dimethylphenol, methyl salicylate, 3,5 dichlorophenol, p-nitrophenol, p-bromophenol. The enhancer is present in an amount of from about 0.4% to about 20% by weight of the developer solution. Preferably the enhancer is present from about 1% to about 10% by weight of the developer.

The developing solution is largely alcoholic. The alcohol employed may be any of the lower alkanols, i.e., containing one to four carbon atoms. The alcohol will be present in an amount of from 60% to about 90% by weight of the developer, preferably from about 70% to about 90%. Advantageously, ethanol is the alcohol employed.

The stabilized hydrogen peroxide will be present from about 1% to about 10% by weight, preferably from about 3% to about 6% by weight of the developing solution.

Water will be present from about 7% to about 23% by weight, preferably from about 7% to about 14% by weight of the developing solution.

Tests were conducted to demonstrate the advantages of the novel developing solution of this invention over the conventional developer employed in the fecal occult blood tests. These tests were performed by spiking fecal samples with various concentrations of blood. Whole blood in the amounts of 0, 0.2, 0.5 and 1 ml of blood were added to 100 gm of feces. Horseradish peroxidase was also added to fecal samples for this study. The color rating scale employed was as follows.

| SCALE | DESCRIPTION |
|---|---|
| − | No blue color. |
| + | Very faint, barely detectable (trace) blue. Blue color fades rapidly and disappears within one minute. |
| + + | Faint blue color after development. |
| + + + | Distinctly blue color. |
| + + + + | Intense blue color. Wider area of blue color coverage. |

The following examples are intended to illustrate and not to limit the invention in any manner.

EXAMPLE 1

Standard Hemoccult slides containing fecal smears spiked with concentrations of whole blood and horseradish peroxidase as noted below were developed with the commercial developing solution (4–6% hydrogen peroxide in 70% ethanol aqueous solution). Hydrated samples were also prepared by adding one drop of water to the fecal smear. The water was allowed to soak in the smear and the developing solution was added. Following are the results of this test.

| TEST METHOD | SAMPLE BLOOD LEVEL (ml/100 g) | | | | HORSERADISH PEROXIDASE |
|---|---|---|---|---|---|
| | 0 | 0.2 | 0.5 | 1.0 | 3 units/g |
| Hemoccult ® | − | − | ++ | ++ | − |
| Hydrated Hemoccult ® | − | + | +++ | ++++ | ++++ |

The results clearly indicate that although hydrating the fecal smear increases the test sensitivity, its specificity is greatly compromised, i.e., an increase in sensitivity is accompanied by a decrease in specificity.

EXAMPLE 2

The test of Example 1 was repeated employing a developing solution containing an enhancer and comparing the results with the Hemoccult and hydrated Hemoccult slides. The formula of the developing solution was:

| Hydrogen peroxide | 4.0% w/w |
|---|---|
| Methyl paraben* | 8.9% |
| Water | 8.8% |
| Ethanol | 78.3% |

*Methyl parahydroxybenzoate

The following results were obtained.

| TEST METHOD | SAMPLE BLOOD LEVEL (ml/100 g) | | | | HORSERADISH PEROXIDASE |
|---|---|---|---|---|---|
| | 0 | 0.2 | 0.5 | 1.0 | 3 units/g |
| Hemoccult ® | − | − | ++ | ++ | − |
| Hydrated Hemoccult ® | − | + | +++ | ++++ | ++++ |
| Developer + Methyl Paraben | − | +++++ | ++++ | − | |

The results disclose that when an enhancing agent such as methyl paraben is added to the standard developing solution it improved the performance of the test over the standard Hemoccult and hydrated Hemoccult test. Better sensitivity and specificity resulted, i.e., a negative result when peroxidase was present in the feces.

EXAMPLE 3

Tests were conducted to show that the enchancing agent methyl paraben increases the test sensitivity for fecal occult blood when used with different lower alkanol solvent systems. The following results were obtained.

| DEVELOPER SYSTEM* | | SAMPLE BLOOD LEVEL (ml/100 g) | | | | HORSERADISH PEROXIDASE |
|---|---|---|---|---|---|---|
| SOLVENT USED | METHYL PARABEN | 0 | 0.2 | 0.5 | 1.0 | 3 units/g |
| Ethanol | 0 | − | + | +++ | +++ | − |
| Ethanol | 0.5M | − | ++ | ++++ | ++++ | − |
| Methanol | 0 | − | + | +++ | +++ | − |
| Methanol | 0.5M | − | ++ | ++++ | ++++ | − |
| Isopropanol | 0 | − | − | + | ++ | − |
| Isopropanol | 0.5M | − | + | +++ | ++++ | − |
| n-Propanol | 0 | − | − | + | ++ | − |
| n-Propanol | 0.5M | − | + | +++ | ++++ | − |
| 2-Methoxy-ethanol | 0 | − | − | − | + | − |
| 2-Methoxy-ethanol | 0.5M | − | ++ | +++ | ++++ | − |

*For developer systems without methyl paraben, the following composition applies: 4% (w/w) H$_2$O$_2$, 8.8% (w/w) water and 87.2% (w/w) solvent.
*For developer systems with methyl paraben, the following composition applies: 4% (w/w) H$_2$O$_2$, 8.8% (w/w) water, and 8.9% methyl paraben and 78.3 (w/w) solvent.

These results clearly indicate that the use of an enhancer (methyl paraben) results in a more sensitive test in solvent systems using different lower alkanols. The specificity is maintained by all of the solvents systems.

EXAMPLE 4

These tests provide data for different phenolic enhancers in comparison with those for the standard and hydrated Hemoccult. Ethanol was the solvent used in these developing solutions together with 0.5M of enhancer 4% w/w hydrogen peroxide and 8.8% water. The following results were obtained with these tests.

| ENHANCERS USED* | SAMPLE BLOOD LEVEL (ml/100 g) | | | | HORSE-RADISH PEROXIDASE |
|---|---|---|---|---|---|
| | 0 | 0.2 | 0.5 | 1.0 | 3 units/g |
| Hemoccult ® | − | − | ++ | ++ | − |
| Hydrated Hemoccult ® | − | + | +++ | ++++ | ++++ |
| Methyl Paraben | − | ++ | ++++ | ++++ | − |
| Ethyl Paraben | − | ++ | ++++ | ++++ | − |
| n-Propyl Paraben | − | ++ | +++ | ++++ | − |
| n-Butyl Paraben | − | ++ | +++ | ++++ | − |
| Acetaminophen | − | ++ | ++++ | ++++ | − |
| 4-Hydroxy-3-methoxy benzonitrile | − | ++ | ++++ | ++++ | − |
| 2,4,6-Tribromophenol | − | + | +++ | ++++ | − |
| p-Hydroxydiphenol | − | ++ | ++++ | ++++ | − |
| p-Nitrophenol | − | + | +++ | ++++ | − |
| Phenol | − | + | +++ | ++++ | − |
| Guaiacol | − | + | ++++ | ++++ | − |
| p-Hydroxy-benzoic Acid | − | + | +++ | ++++ | − |
| 3,5-Dimethylphenol | − | + | +++ | ++++ | − |
| 2,6-Dimethylphenol | − | + | ++ | +++ | − |
| Methyl salicylate | − | + | +++ | ++++ | − |
| 3,5-Dichlorophenol | − | ++ | +++ | ++++ | − |
| 3,4-Dichlorophenol | − | + | ++++ | ++++ | − |
| B-Naphthol | − | + | ++++ | ++++ | − |
| p-Cyanophenol | − | ++ | +++ | ++++ | − |

| ENHANCERS USED* | SAMPLE BLOOD LEVEL (ml/100 g) | | | | HORSE-RADISH PEROX-IDASE |
|---|---|---|---|---|---|
| | 0 | 0.2 | 0.5 | 1.0 | 3 units/g |
| p-Bromophenol | − | ++ | ++++ | ++++ | − |

These results disclose that when any of the above enhancers are present in the developing solution a more sensitive test results when compared to the standard Hemoccult. The hydrated Hemoccult results in a sensitive test but loses its specificity by getting false positive results with horseradish peroxidase.

In summary, the results of the above tests, Examples 1–4, demonstrate that by employing the novel developing solution of this invention the overall performance of the standard fecal occult blood test (Hemoccult) was greatly improved. The results disclose improved sensitivity while maintaining or improving specificity. Lower blood levels were detected in the feces. The samples with the same blood levels had greater readability, i.e. deeper blue color, than the standard Hemoccult.

While the invention has been described and illustrated with respect to specific embodiments, it is to be understood that modifications and equivalents may be apparent to those skilled in the art and are intended to be within the scope of the invention. References set forth in the background of invention are incorporated herein by reference.

We claim:

1. In a fecal occult blood test using a solid test matrix containing guaiac having a fecal smear applied to said matrix and an alcoholic hydrogen peroxide developing solution placed on said smear, the improvement comprising said developing solution additionally containing a phenolic enhancing compound before said developing solution is placed on said matrix having a fecal smear.

2. The test of claim 1 wherein said enhancer is an ester of hydroxybenzoic acid.

3. The test of claim 1 wherein said enhancer is a para-hydroxybenzoate derivative.

4. The test of claim 3 wherein said derivative is selected from the group consisting of methyl, ethyl, propyl and butyl parahydroxybenzoate.

5. The test of claim 4 wherein said enhancer is ethyl parahydroxybenzoate.

6. The test of claim 1 wherein said alcohol is selected from the group consisting of methanol, ethanol and propanol.

* * * * *